(12) United States Patent
Welinder et al.

(10) Patent No.: US 9,928,278 B2
(45) Date of Patent: *Mar. 27, 2018

(54) SYSTEMS AND METHODS FOR DISTRIBUTED DATA ANNOTATION

(71) Applicant: California Institute of Technology, Pasadena, CA (US)

(72) Inventors: Peter Welinder, San Diego, CA (US); Pietro Perona, Altadena, CA (US)

(73) Assignee: California Institute of Technology, Pasadena, CA (US)

( * ) Notice: Subject to any disclaimer, the term of this patent is extended or adjusted under 35 U.S.C. 154(b) by 790 days.

This patent is subject to a terminal disclaimer.

(21) Appl. No.: 14/198,873

(22) Filed: Mar. 6, 2014

(65) Prior Publication Data
US 2014/0188879 A1 Jul. 3, 2014

Related U.S. Application Data

(63) Continuation of application No. 13/651,108, filed on Oct. 12, 2012, now Pat. No. 8,706,729.
(Continued)

(51) Int. Cl.
*G06F 17/30* (2006.01)
*G06Q 10/10* (2012.01)
*G06Q 50/24* (2012.01)

(52) U.S. Cl.
CPC ...... *G06F 17/30525* (2013.01); *G06F 17/301* (2013.01); *G06F 17/30864* (2013.01);
(Continued)

(58) Field of Classification Search
CPC ............. G06F 17/30525; G06F 17/301; G06F 17/30997; G06Q 50/24; G06Q 10/101
See application file for complete search history.

(56) References Cited

U.S. PATENT DOCUMENTS 6,636,843 B2 10/2003 Doddi et al.
6,897,875 B2 5/2005 Zhang
(Continued)

OTHER PUBLICATIONS

Antoniak, "Mixtures of Dirchlet Processes with Applications to Bayesian Nonparametric Problems", The Annals of Statistics, 1974, vol. 2, No. 6, pp. 1152-1174.
(Continued)

*Primary Examiner* — Scott A Waldron
*Assistant Examiner* — Andalib Lodhi
(74) *Attorney, Agent, or Firm* — KPPB LLP

(57) ABSTRACT

Systems and methods for distributed data annotation in accordance embodiments of the invention are disclosed. In one embodiment of the invention, a distributed data annotation server system includes a storage device configured to store source data, one or more annotators, annotation tasks and a processor, wherein a distributed data annotation application configures the processor to receive source data including one or more pieces of source data, select one or more annotators, create one or more annotation tasks for the selected annotators and source data, request one or more annotations for the source data using the annotation tasks, receive annotations, determine source data metadata for at least one piece of source data using the received annotations, generate annotator metadata for at least one annotator using the received annotations and the source data, and estimate the ground truth for the source data using the source data metadata and the annotator metadata.

21 Claims, 7 Drawing Sheets

Related U.S. Application Data

(60) Provisional application No. 61/546,386, filed on Oct. 12, 2011.

(52) U.S. Cl.
CPC ..... *G06F 17/30997* (2013.01); *G06Q 10/101* (2013.01); *G06Q 50/24* (2013.01); *G06F 17/30011* (2013.01); *G06F 17/30867* (2013.01)

(56) References Cited

U.S. PATENT DOCUMENTS

| | | | |
|---|---|---|---|
| 7,610,130 B1 | 10/2009 | Dixon et al. | |
| 7,809,722 B2 | 10/2010 | Gokturk et al. | |
| 7,987,186 B1 | 7/2011 | Joshi | |
| 8,041,568 B2 | 10/2011 | Strope et al. | |
| 8,418,249 B1 | 4/2013 | Nucci et al. | |
| 8,818,793 B1 | 8/2014 | Bangalore et al. | |
| 8,849,648 B1 | 9/2014 | Bangalore et al. | |
| 9,239,848 B2 * | 1/2016 | Liu | G06F 17/30247 |
| 9,344,466 B1 * | 5/2016 | Abuzalaf | H04W 4/00 |
| 9,355,167 B2 | 5/2016 | Gomes et al. | |
| 9,355,359 B2 | 5/2016 | Welinder et al. | |
| 9,355,360 B2 | 5/2016 | Welinder et al. | |
| 9,483,794 B2 * | 11/2016 | Amtrup | G06Q 20/3276 |
| 9,704,106 B2 | 7/2017 | Welinder et al. | |
| 9,898,701 | 2/2018 | Welinder et al. | |
| 2006/0129596 A1 * | 6/2006 | Bays | G06F 17/241 |
| 2008/0005064 A1 | 1/2008 | Sarukkai et al. | |
| 2008/0016102 A1 * | 1/2008 | Albornoz | G06F 17/30997 |
| 2010/0023553 A1 * | 1/2010 | Gausman | G06F 17/30038 707/E17.009 |
| 2011/0274334 A1 * | 11/2011 | Zhu | G06T 7/204 382/132 |
| 2012/0158620 A1 * | 6/2012 | Paquet | G06N 99/005 706/12 |
| 2012/0221508 A1 | 8/2012 | Chaturvedi et al. | |
| 2013/0024457 A1 | 1/2013 | Chua et al. | |
| 2013/0031457 A1 | 1/2013 | Griffiths et al. | |
| 2013/0080422 A1 | 3/2013 | Pan | |
| 2013/0097164 A1 | 4/2013 | Welinder et al. | |
| 2014/0289246 A1 | 9/2014 | Gomes et al. | |
| 2014/0304270 A1 | 10/2014 | Torkamani et al. | |
| 2016/0275173 A1 | 9/2016 | Gomes et al. | |
| 2016/0275417 A1 | 9/2016 | Welinder et al. | |
| 2016/0275418 A1 | 9/2016 | Welinder et al. | |

OTHER PUBLICATIONS

Attias, "A Variational Bayesian Framework for Graphical Models", NIPS, 1999, pp. 209-215.

Bennett, "Using Asymmetric Distributions to Improve Classifier Probabilities: A Comparison of New and Standard Parametric Meethods", Technical report, Carnegie Mellon University, 2002, 24 pgs.

Berg et al., "Automatic Attribute Discovery and Characterization from Noisy Web Data", Computer Vision—ECCV 2010, pp. 663-676.

Beygelzimer et al., "Importance Weighted Active Learning", Proceedings of the 26th International Conference on Machine Learning, 2009, 8 pgs.

Bourdev et al., "Poselets: Boyd Part Detectors Trained Using 3D Human Pose Annotations", ICCV, 2009, 42 pgs.

Byrd et al., "A Limited Memory Algorithm for Bound Constrained Optimization", SIAM Journal on Scientific and Statistical Computing, 1995, vol. 16, No. 5, pp. 1190-1208.

Cohn et al., "Active Learning with Statistical Models", Journal of Artificial Intelligence Research, 1996, vol. 4, pp. 129-145.

Dalal et al., "Histograms of Oriented Gradients for Human Detection", ICCV, 2005, 8 pgs.

Dankert et al., "Automated Monitoring and Analysis of Social Behavior in *Ddrosophila*", Nat. Methods, Apr. 2998, vol. 6, No. 4, 17 pgs.

Dasgupta et al., "Hierarchical Sampling for Active Learning", ICML, 2008, 8 pgs.

Dawid et al., "Maximum Likelihood Estimation of Observer Error-rates using the EM Algorithm", J. Roy. Statistical Society, Series C, 1979, vol. 28, No. 1, pp. 20-28.

Deng et al., "ImageNet: A Large-Scale Hierarchical Image Database", CVPR, 2009, 8 pgs.

Dollar et al., "Cascaded Pose Regression", CVPR, 2010, pp. 1078-1085.

Dollar et al., "Pedestrian Detection: An Evaluation of the State of the Art", IEEE Transactions on Pattern Analysis and Machine Intelligence, 2011, 20 pgs.

Erkanli et al., "Bayesian semi-parametric ROC analysis", Statistics in Medicine, 2006, vol. 25, pp. 3905-3928.

Fei-Fei et al., "A Bayesian Hierarchical Model for Learning Natural Scene Categories", CVPR, IEEE Computer Society, 2005, pp. 524-531.

Frank et al., "UCI Machine Learning Repository", 2010, 3 pgs.

Fuchs et al., "Randomized tree ensembles for object detection in computational pathology", Lecture Notes in Computer Science, ISVC, 2009, vol. 5875, pp. 367-378.

Gionis et al., "Clustering Aggregation", ACM Transactions on Knowledge Discovery from Data, 2007. vol. 1, 30 pgs.

Gomes, et al., "Crowdclustering", Technical Report, Caltech 20110628-202526159, Jun. 2011, 14 pgs.

Gomes et al., "Crowdclustering", Technical Report, Caltech, 2011, pp. 558-561.

Gu et al, "Bayesian bootstrap estimation of ROC curve", Statistics in Medicine, 2008, vol. 27, pp. 5407-5420.

Hellmich et al., "Bayesian Approaches to Meta-analysis of ROC Curves", Med. Decis. Making, Jul.-Sep. 1999, vol. 19, pp. 252-264.

Jaakkola et al., "A variational approach to Bayesian logistic regression models and their extensions", Source unknown, Aug. 13, 1996, 10 pgs.

Kruskal, "Multidimensional Scaling by Optimizing Goodness of Fit to a Nonmetric Hypothesis", Psychometrika, Mar. 1964. vol. 29, No. 1, pp. 1-27.

Kurihara et al., "Accelerated Variational Dirichlet Process Mixtures", Advances in Neural Information Processing Systems, 2007, 8 pgs.

Li et al., "Solving consensus and Semi-supervised Clustering Problems Using Nonnegative Matrix Factorization", ICDM, IEEE computer society 2007. pp. 577-582.

Little et al., "Exploring Iterative and Parallel Human Computational Processes", HCOMP, 2010, pp. 68-76.

Little et al., "TurKit: Tools for Iterative Tasks on Mechanical Turk", HCOMP, 2009, pp. 29-30.

Maceachern et al., "Estimating Mixture of Dirichlet Process Models", Journal of Computational and Graphical Statistics, Jun. 1998, vol. 7, No. 2, pp. 223-238.

Mackay, "Information-Based Objective Functions for Active Data Selection", Neural Computation, 1992, vol. 4, pp. 590-604.

Martinez-Munoz et al., "Dictionary-Free Categorization of Very Similar Objects via Stacked Evidence Trees", Source unknown, 2009, 8 pgs.

Meila, "Comparing Clusterings by the Variation of Information", Learning theory and Kernel machines: 16th Annual Conference of Learning Theory and 7th Kernel Workshop, COLT/Kernel 2003, 31 pgs.

Monti et al., "Consensus Clustering: A Resampling-Based Method for Class Discovery and Visualization of Gene Expression Microarray Data", Machine Learning, 2003, vol. 52, pp. 91-118.

Neal, "MCMC Using Hamiltonian Dynamics", Handbook of Markov Chain Monte Carlo, 2010, pp. 113-162.

Nigam et al., "Text Classification from labeled and Unlabeled Documents Using EM", Machine Learning, 2000, vol. 39, No. 2/3, pp. 103-134.

Platt, "Probalisitic Outputs for Support Vector Machines and Comparisons to Regularized Likelihood Methods", Advances in Large Margin Classiers, 1999, MIT Press, pp. 61-74.

(56) References Cited

OTHER PUBLICATIONS

Raykar et al., "Supervised Learning from Multiple Experts: Whom to trust when everyone lies a bit", ICML, 2009, 8 pgs.
Russell et al., "LabelMe: A Database and Web-Based Tool for Image Annotation", Int. J. Comut. Vis., 2008, vol. 77, pp. 157-173.
Seeger, "Learning with labeled and unlabeled data", Technical Report, University of Edinburgh, 2002, 62 pgs.
Sheng et al., "Get Another Label? Improving Data Quality and Data Mining Using Multiple, Noisy Labelers", KDD, 2008, 9 pgs.
Smyth et al., "Inferring Ground Truth from Subjective Labelling of Venus Images", NIPS, 1995, 8 pgs.
Snow et al., "Cheap and Fast—But is it Good? Evaluating Non-Expert Annotations for Natural Language Tasks", EMNLP, 2008, 10 pgs.
Sorokin et al., "Utility data annotation with Amazon Mechanical Turk", First IEEE Workshop on Internet Vision at CVPR '08, 2008, 8 pgs.
Spain et al., "Some objects are more equal than others: measuring and predicting importance", ECCV, 2008, 14 pgs.
Strehl et al., "Cluster Ensembles—A Knowledge Reuse Framework for Combinint Multiple Partitions", Journal of Machine Learning Research, 2002, vol. 3, pp. 583-617.
Tong et al, "Support Vector Machine Active Learning with Applications to Text Classification", Journal of Machine Learning Research, 2001, pp. 45-66.
Vijayanarasimhan et al, "Large-Scale Live Active Learning: Training Object Detectors with Crawled Data and Crowds", CVPR, 2001, pp. 1449-1456.
Vijayanarasimhan et al., "What's It Going to Cost You?: Predicting Effort vs. Informataiveness for Multi-Label Image Annotations", CVPR, 2009, pp. 2262-2269.
Von Ahn et al., "Labeling Images with a Computer Game", SIGCHI conference on Human factors in computing systems, 2004, pp. 319-326.
Von Ahn et al., "reCAPTCHA: Human-Based Character Recognition via Web Security Measures", Science, 2008, vol. 321, No. 5895, pp. 1465-1468.
Vondrick et al, "Efficiently Scaling up Video Annotation with Crowdsourced Marketplaces", ECCV, 2010, pp. 610-623.
Welinder et al., "Caltech-UCSD Birds 200", Technical Report CNS-TR-2010-001, 2001, 15 pgs.
Welinder et al., "Online crowdsourcing: rating annotators and obtaining.cost-effective labels", IEEE Conference on Computer Vision and Pattern Recognition Workshops (ACVHL), 2010, pp. 25-32.
Welinder et al., "The Multidimensional Wisdom of Crowds", Neural Information Processing Systems Conference (HIPS), 2010, pp. 1-9.
Whitehill et al, "Whose Vote Should Count More: Optimal Integration of Labels from Labelers of Unknown Expertise", NIPS, 2009, 9 pgs.
Zhu, "Semi-Supervised Learning Literature Survey", Technical report, University of Wisconsin-Madison, 2008, 60 pgs.
Bitton, E., "Geometric Models for Collaborative Search and Filtering", 2011, 186 pages.
Ertekin, S. et al., "Learning to predict the wisdom of crowds", arXiv preprint arXiv:1204.3611 v1, Apr. 16, 2012, 8 Pages.
Ertekin, S. et al., "Wisely Using a Budget for Crowdsourcing", or 392-12. Massachusetts Institute of Technology, Apr. 2012, 31 pages.
Zhao, L. et al., "Robust Active Learning Using Crowdsourced Annotations for Activity Recognition", In Human Computation: Papers from the 2011 All Workshop, Jan. 2011, pp. 74-79.

* cited by examiner

SYSTEMS AND METHODS FOR DISTRIBUTED DATA ANNOTATION

CROSS-REFERENCE TO RELATED APPLICATIONS

The current application is a continuation of U.S. patent application Ser. No. 13/651,108, filed Oct. 12, 2012, that claims priority to U.S. Provisional Patent Application No. 61/546,386, titled "Algorithm for Estimating for Annotator Expertise, Bias and Competence and Image Difficulty in Binary Image Annotation" and filed Oct. 12, 2011, the disclosures of which are incorporated herein by reference in their entirety.

FEDERAL FUNDING SUPPORT

This invention was made with government support under AGS0941760 awarded by the National Science Foundation and under N00014-08-1-0638; N00014-06-1-0734 awarded by the NAVY. The government has certain rights in the invention.

FIELD OF THE INVENTION

The present invention is generally related to data annotation and more specifically the distributed annotation of pieces of data contained in data sets.

BACKGROUND OF THE INVENTION

Amazon Mechanical Turk is a service provided by Amazon.com of Seattle, Wash. Amazon Mechanical Turk provides the ability to submit tasks and have a human complete the task in exchange for a monetary reward for completing the task.

SUMMARY OF THE INVENTION

Systems and methods for distributed data annotation in accordance embodiments of the invention are disclosed. In one embodiment of the invention, a distributed data annotation server system includes at least one storage device configured to store source data, one or more annotators, annotation tasks, and a distributed data annotation application and a processor, wherein the distributed data annotation application configures the processor to receive source data, where the source data includes one or more pieces of source data, select one or more annotators for at least one piece of source data, create one or more annotation tasks for the selected annotators and at least one piece of source data, request one or more annotations for at least one piece of source data using the created annotation tasks, receive annotations for at least one piece of source data, determine source data metadata for at least one piece of source data using the received annotations, where the source data metadata includes source data characteristics, generate annotator metadata for at least one annotator using the received annotations and at least one piece of source data, where the annotator metadata includes identified annotator characteristics, and estimate the ground truth for at least one piece of source data using the source data metadata and the annotator metadata.

In another embodiment of the invention, the distributed data annotation application further configures the processor to estimate the ground truth for at least one piece of source data using the source data metadata and the annotator metadata by iteratively updating source data metadata for at least one piece of source data based upon at least the previously generated source data metadata and annotator metadata, updating annotator metadata for at least one annotator based upon at least the previously generated source data metadata and annotator metadata, and estimating the ground truth for at least one piece of source data using the updated source data metadata and the updated annotator metadata when a termination condition occurs.

In an additional embodiment of the invention, the distributed data annotation application configures the processor to determine source data characteristics in the source data metadata and identify annotator characteristics in the annotator metadata using an iterative maximum a posteriori estimation and the received annotations.

In yet another additional embodiment of the invention, the iterative maximum a posteriori estimation is selected from the group consisting of gradient ascent, gradient descent, and estimation-maximization.

In still another additional embodiment of the invention, the distributed data annotation application further configures the processor to update source data metadata for at least one piece of source data using the received annotations and the annotator metadata.

In yet still another additional embodiment of the invention, the source data metadata includes a measure of the difficulty of describing the source data.

In yet another embodiment of the invention, the source data metadata further includes source data characteristics selected from the group consisting of annotations applied to the piece of source data, features of the source data, and annotators who have previously annotated the piece of source data.

In still another embodiment of the invention, the distributed data annotation application further configures the processor to update annotator metadata for at least one annotator using the received annotations and the source data metadata.

In yet still another embodiment of the invention, the annotator metadata includes a measure of the competence of the annotator In yet another additional embodiment of the invention, the annotator metadata further includes annotator characteristics selected from the group consisting of the expertise of the annotator, the bias of the annotator regarding mislabeling of source data, annotations previously provided by the annotator, and references to source data previously annotated by the annotator.

In still another additional embodiment of the invention, the distributed data annotation application further configures the processor to determine a confidence threshold value regarding the ground truth of at least one piece of source data.

In yet still another additional embodiment of the invention, the distributed data annotation software further configures the processor to determine a cost for performing the annotation task.

In yet another embodiment of the invention, the annotation task is a human intelligence task and the distributed data annotation software further configures the processor to request one or more annotations by submitting at least one annotation task to a human intelligence task marketplace.

In still another embodiment of the invention, the annotation task is a machine intelligence task and the distributed data annotation software further configures the processor to request one or more annotations by submitting at least one annotation task to an annotation device configured to perform machine intelligence tasks.

In yet still another embodiment of the invention, selecting one or more annotators for at least one piece of source data includes selecting one or more annotators based on at least one annotator characteristic in the annotator metadata describing the one or more annotators.

In yet another additional embodiment of the invention, selecting one or more annotators for at least one piece of source data includes selecting one or more annotators based on at least one source data characteristic in the source data metadata.

Yet another embodiment of the invention includes a method for distributed data annotation including receiving source data using a distributed data annotation server system, where the source data includes one or more pieces of source data, selecting one or more annotators for at least one piece of source data using the distributed data annotation server system, creating one or more annotation tasks for the selected annotators and at least one piece of source data using the distributed data annotation server system, requesting one or more annotations for at least one piece of source data using the created annotation tasks and the distributed data annotation server system, receiving annotations for at least one piece of source data using the distributed data annotation server system, determining source data metadata for at least one piece of source data using the received annotations and the distributed data annotation server system, where the source data metadata includes source data characteristics, generating annotator metadata for at least one annotator using the received annotations, at least one piece of source data, and the distributed data annotation server system, where the annotator metadata includes identified annotator characteristics, and estimating the ground truth for at least one piece of source data using the source data metadata, the annotator metadata, and the distributed data annotation server system.

In yet another additional embodiment of the invention, estimating the ground truth for at least one piece of source data using the source data metadata and the annotator metadata further includes iteratively updating source data metadata for at least one piece of source data using the distributed data annotation server system based upon at least the previously generated source data metadata and annotator metadata, updating annotator metadata for at least one annotator and the distributed data annotation server system based upon at least the previously generated source data metadata and annotator metadata, and estimating the ground truth for at least one piece of source data using the distributed data annotation server system based upon the updated source data metadata and the updated annotator metadata when a termination condition occurs.

In still another additional embodiment of the invention, distributed data annotation further comprising determining source data characteristics in the source data metadata and identifying annotator characteristics in the annotator metadata using an iterative maximum a posteriori estimation, the received annotations, and the distributed data annotation server system.

In yet still another additional embodiment of the invention, the iterative maximum a posteriori estimation is selected from the group consisting of gradient ascent, gradient descent, and estimation-maximization.

In yet another embodiment of the invention, distributed data annotation updating source data metadata for at least one piece of source data using the received annotations, the annotator metadata, and the distributed data annotation server system.

In still another embodiment of the invention, the source data metadata includes a measure of the difficulty of describing the source data.

In yet still another embodiment of the invention, the source data metadata further includes source data characteristics selected from the group consisting of annotations applied to the piece of source data, features of the source data, and annotators who have previously annotated the piece of source data.

In yet another additional embodiment of the invention, distributed data annotation further comprising updating annotator metadata for at least one annotator using the received annotations, the source data metadata, and the distributed data annotation server system.

In still another additional embodiment of the invention, the annotator metadata includes a measure of the competence of the annotator In yet still another additional embodiment of the invention, the annotator metadata further includes annotator characteristics selected from the group consisting of the expertise of the annotator, the bias of the annotator regarding mislabeling of source data, annotations previously provided by the annotator, and references to source data previously annotated by the annotator.

In yet another embodiment of the invention, distributed data annotation further comprising determining a confidence threshold value regarding the ground truth of at least one piece of source data using the distributed data annotation server system.

In still another embodiment of the invention, distributed data annotation further comprising determining a cost for performing the annotation task using the distributed data annotation server system.

In yet still another embodiment of the invention, the annotation task is a human intelligence task and requesting one or more annotations further includes submitting at least one annotation task to a human intelligence task marketplace using the distributed data annotation server system.

In yet another additional embodiment of the invention, the annotation task is a machine intelligence task and requesting one or more annotations further includes submitting at least one annotation task to an annotation device using the distributed data annotation server system, where the annotation device is configured to perform machine intelligence tasks.

In still another additional embodiment of the invention, selecting one or more annotators for at least one piece of source data includes selecting one or more annotators based on at least one annotator characteristic in the annotator metadata describing the one or more annotators using the distributed data annotation server system.

In yet still another additional embodiment of the invention, selecting one or more annotators for at least one piece of source data includes selecting one or more annotators based on at least one source data characteristic in the source data metadata using the distributed data annotation server system.

Still another embodiment of the invention includes a distributed data annotation server system including at least one storage device configured to store source data, one or more annotators, annotation tasks, and a distributed data annotation application and a processor, wherein the distributed data annotation application configures the processor to receive source data, where the source data includes one or more pieces of source data, select one or more annotators for at least one piece of source data, create one or more annotation tasks for the selected annotators and at least one piece of source data, request one or more annotations for at least one piece of source data using the created annotation tasks, receive annotations for at least one piece of source data, and perform an iterative a posteriori estimation of the ground truth for at least one piece of source data, the difficulty of describing the at least one piece of source data and the competence of the selected annotators that annotated the at least one piece of source data based upon the received annotations.

DETAILED DESCRIPTION

Figure 1:
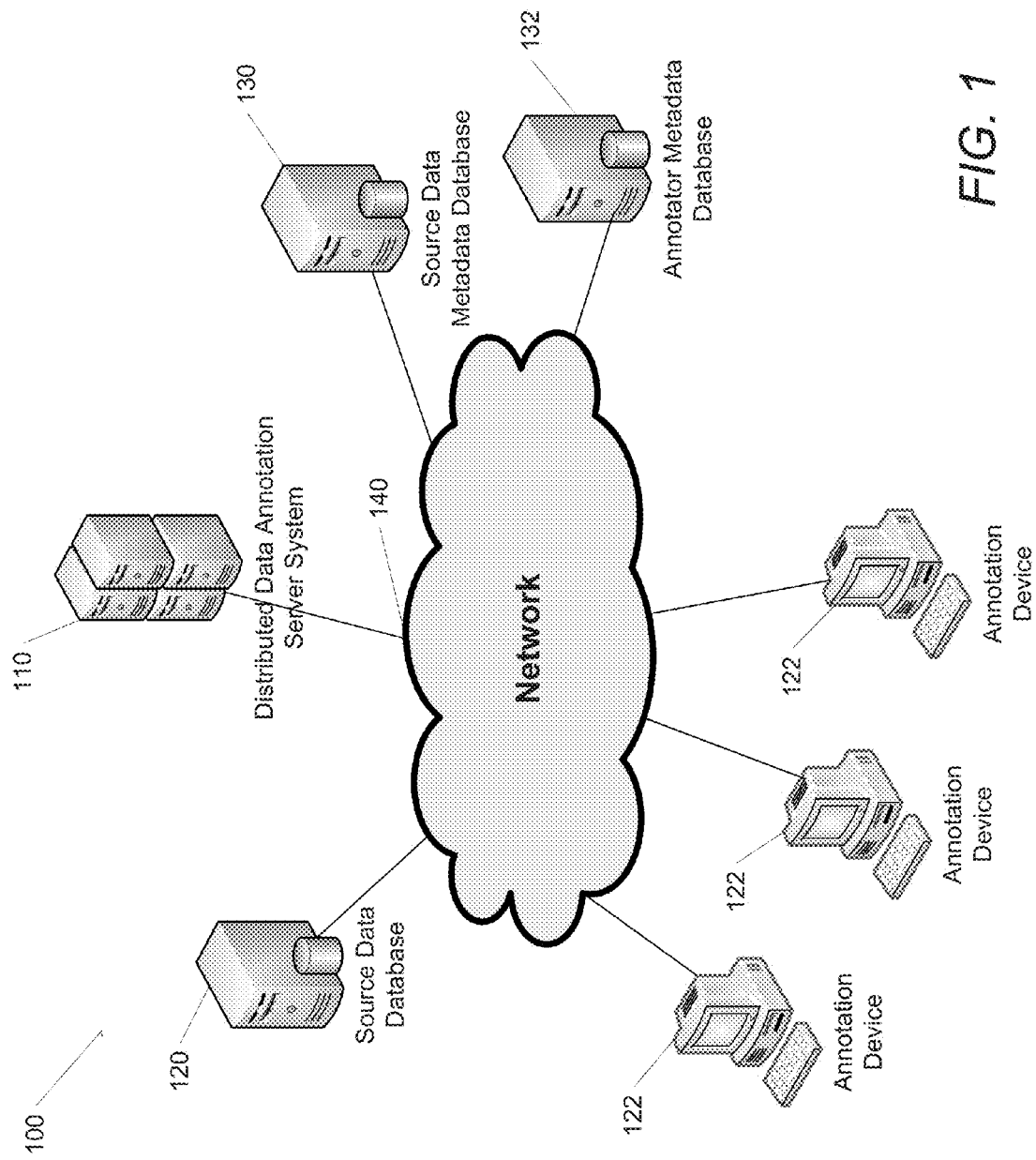
FIG. 1 conceptually illustrates a distributed data annotation system in accordance with an embodiment of the invention.

Turning now to the drawings, systems and methods for distributed data annotation in accordance with embodiments of the invention are illustrated. Producing accurate annotations for a variety of source data is vital for many applications, including, but not limited to, medical diagnosis, surveillance verification, performing data de-duplication, transcribing audio recordings, or researching data details. Commonly, the annotation of source data is performed as a human intelligence task with the corresponding expense and risk of inaccuracy attributable to human intelligence tasks. Services such as Amazon Mechanical Turk (MTurk) facilitate the distribution of annotation tasks to one or more annotators. The correctness of the annotations as provided by the annotators can be determined in a variety of ways, including collecting several annotations for each piece of source data and determining the correct annotation based upon the most commonly occurring annotation. In accordance with many embodiments of the invention, a correct annotation for a piece of source data corresponds to the ground truth for the information represented in the piece of source data. However, relying upon a majority of annotations to determine the ground truth for a piece of source data has several limitations, including the duplication of annotation work which increases the amount of time and money necessary to determine the annotations, the fact that a majority vote as to the ground truth for a piece of source data may not result in the correct ground truth being identified, and uncertainty as to what the majority vote is for a particular piece of source data, particularly when there are several annotations relatively equally applied to a piece of source data by the annotators.

Distributed data annotation systems in accordance with embodiments of the invention are configured to annotate pieces of source data and to determine annotator characteristics describing the annotators annotating the pieces of source data. In many embodiments, the annotations applied to a piece of source data include a label describing the ground truth of the content contained in the piece of source data. Annotator quality and ability can vary between annotators; some annotators are more skilled and consistent in their annotations than others. Some annotators may be adversarial and intentionally provide incorrect or misleading annotations. Additionally, some annotators may have more skill or knowledge about the information contained in the pieces of source data than other annotators.

Distributed data annotation systems in accordance with many embodiments of the invention generate multidimensional models of annotators representing a variety of attributes of a particular annotator. Annotator multidimensional models include a variety of attributes including, but not limited to, the skill of a particular annotator in providing labels, annotator bias, and the knowledge of the annotator.

In several embodiments, distributed data annotation systems can be configured to generate a multidimensional model for pieces of source data. The source data multidimensional model can include a variety of attributes, including, but not limited to, the annotation for the piece of source data and the difficulty associated with determining the annotation for the piece of source data. Different pieces of source data may be easier or more difficult to annotate; that is, it may be easier for annotators to identify the ground truth for some pieces of source data, while annotators (at all skill levels) may struggle with identifying the ground truth for other pieces of data. Furthermore, annotators may be consistent in their annotation of related pieces of data; that is, one annotator may be competent in identifying the pieces of data and provide consistently correct annotations, while another annotator may be incompetent in identifying the pieces of data and provide consistently incorrect annotations for the pieces of data.

Utilizing a source data multidimensional model and an annotator multidimensional model, a distributed data annotation system in accordance with embodiments of the invention can accurately determine the ground truth for a piece of source data in a manner that accounts for the abilities of specific annotators used to annotate the source data and/or the difficulty of annotating specific pieces of source data. In a variety of embodiments, distributed data annotation systems utilize an annotator multidimensional model and a source data multidimensional model to select annotators to task with annotating pieces of source data in order to determine the most accurate annotations for a piece of source data using as few of annotators as possible. For example, using the annotator multidimensional model and the source data multidimensional model, a distributed data annotation system can generate a competence measure for an annotator with respect to a piece of source data or set of source data. If the competence measure exceeds a competence threshold value, the distributed data annotation system can request an annotation from the annotator for the piece of source data or one or more pieces of source data within the set of source data. Likewise, if the competence measure falls below an incompetence threshold value, the annotator will be disqualified from providing an annotation for the source data. Systems and methods for distributed data annotation in accordance with embodiments of the invention are discussed further below.

Distributed Data Annotation Systems

Distributed data annotation systems in accordance with embodiments of the invention are configured to assign a set of source data for a set of annotators to annotate and, based on the annotations, can determine a variety of characteristics for both the source data and the annotators. Based upon the determined characteristics of the source data and the annotators, the distributed data annotation system can estimate ground truths for the source data. A conceptual illustration of a distributed data annotation system in accordance with an embodiment of the invention is shown in FIG. 1. The distributed data annotation system 100 includes a distributed data annotation server system 110 connected to a source data database 120, one or more annotation devices 122, a source data metadata database 130, and an annotator metadata database 132 via a network 140.

The source data database 120 includes one or more sets of source data to be annotated using the distributed data annotation server system 110. A set of source data includes one or more pieces of source data. Pieces of source data include, but are not limited to, image data, audio data, and text data. In several embodiments, one or more pieces of source data in the source data database 120 include metadata describing the piece of source data. The distributed data annotation server system 110 is configured to receive annotations from annotation devices 122. Annotation devices 122 are configured to receive annotations for one or more pieces of data from a variety of sources, including, but not limited to, human annotators, machine annotators, and emulations of human annotators performed using machines. The annotation devices 122 transmit those annotations to the distributed data annotation server system 110. In the illustrated embodiment, the annotation devices are illustrated as personal computers configured using appropriate software. In various embodiments, annotation devices can include (but are not limited to) tablet computers, mobile phone handsets, and any of a variety of network-connected devices.

The distributed data annotation server system 110 is configured to assign one or more pieces of source data contained in the source data database 120 to one or more annotators using source data metadata associated with the assigned piece of source data and/or the annotator metadata associated with the annotator. Annotators can utilize annotation devices 122 to authenticate themselves to the distributed data annotation server system 110, access assigned source data, and provide annotations with respect to the assigned pieces of source data. The distributed data annotation server system 110 receives one or more annotations for pieces of source data from the annotation devices 122 and generates source data metadata associated with the pieces of source data using the received annotations. In many embodiments, the source data metadata is stored in source data metadata database 130. In several embodiments, the metadata is associated with and/or included within the files containing the pieces of source data. The distributed data annotation server system 110 is further configured to generate annotator metadata describing the characteristics of one or more of the annotators corresponding to the received annotations and store the annotator metadata in the annotator metadata database 132. In the illustrated embodiment, the source data metadata and the annotator metadata are shown as stored in separate databases. In a number of embodiments, the source data metadata and the annotator metadata can be stored in a single database or across multiple databases as appropriate to the requirements of a specific application. In a variety of embodiments, the distributed data annotation server system 110 includes a control console configured to receive input to define and initiate the distributed data annotation process. In several embodiments, the distributed data annotation server system 110 is configured to output the results of the distributed data annotation process using the control console.

In many embodiments, source data metadata contains data describing source data characteristics for a piece of source data. Source data characteristics can include, but are not limited to, the difficulty of the piece of source data, annotations provided for the piece of source data, and the estimated ground truth of the piece of source data. In a number of embodiments, annotator metadata contains data describing annotator characteristics for an annotator. Annotator characteristics include, but are not limited to, the skill of the annotator, the competence of the annotator, and pieces of data annotated by the annotator. As is discussed further below, annotator characteristics for a specific annotator can be determined by observation of the annotations made by the annotator in the context of annotations made by other annotators and the difficulty associated with annotating the annotated pieces of data. In accordance with many embodiments of the invention, the distributed data annotation server system 110 is configured to update source data metadata and/or annotator metadata as additional annotations are received from annotators via annotation devices 112.

In a number of embodiments, annotation of data is performed in a similar manner to classification via a taxonomy in that an initial distributed data annotation is performed using broad categories and metadata is collected concerning the difficulty of annotating the pieces of source data and the capabilities of the annotators. Each of the initial broad categories can then be farmed out to annotators by the distributed data annotation server 110 to further refine the source data metadata associated with each piece of source data in the broad categories and the process repeated until sufficient metadata describing the source data is collected. With each pass across the data by the annotators, the distributed data annotation server system 110 can use the received annotations for one or more pieces of source data to refine the descriptions of the characteristics of the annotators and the updated descriptions can be stored as annotator metadata in the annotator metadata database 132. Based upon the updated annotator metadata, the distributed data annotation server system 110 can further refine the selection of annotators to utilize for subsequent annotation of the source data. Although specific taxonomy based approaches for annotating source data with increased specificity are discussed above, any of a variety of techniques can be utilized to annotate source data including techniques that involve a single pass or multiple passes by the same set of annotators or different sets of annotators as appropriate to the requirements of specific applications in accordance with embodiments of the invention.

In a variety of embodiments, the distributed data annotation server system 110 is configured to determine a ground truth value for one or more pieces of source data using source data metadata and/or annotator metadata. In many embodiments, the distributed data annotation server system 110 is configured to update the source data metadata and/or the annotator metadata based upon the determined ground truth value for one or more pieces of source data. In a number of embodiments, the distributed data annotation server system 110 is configured to refine the ground truth value for a piece of data, the source data metadata, and/or the annotator metadata as the ground truth values, source data metadata, and/or annotator metadata is updated. In several embodiments, the refinement continues until at least one of the values converges within a threshold value and/or a predetermined number of iterations are exceeded. In many embodiments, an appropriate threshold value can be determined dynamically or is pre-determined.

In many embodiments, the distributed data annotation server system 110, source data database 120, source data metadata database 130, and annotator metadata database 132 are implemented using a single server. In a variety of embodiments, the distributed data annotation server system 110, source data database 120, source data metadata database 130, and annotator metadata database 132 are implemented using a plurality of servers. The network 140 used to enable devices to communicate can be one or more of a variety of networks, including, but not limited to, a wide-area network, a local area network, and the Internet in accordance with a number of embodiments of the invention.

Distributed data annotation systems in accordance with embodiments of the invention are described above with respect to FIG. 1; however, a variety of distributed data annotations systems can be utilized in accordance with embodiments of the invention. Systems and methods for distributed data annotation in accordance with embodiments of the invention are described below.

Distributed Data Annotation Server Systems

Figure 2:
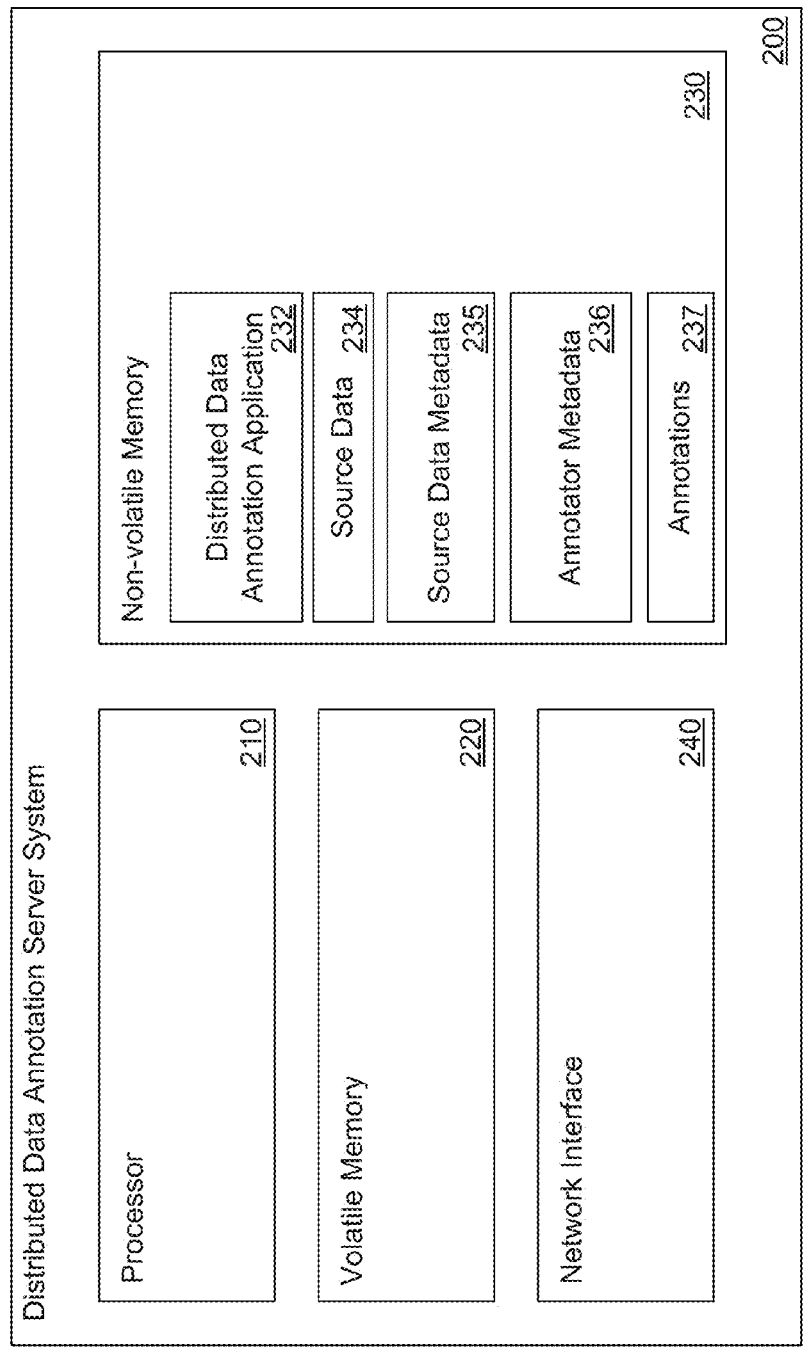
FIG. 2 conceptually illustrates a distributed data annotation server system in accordance with an embodiment of the invention.

Distributed data annotation server systems are configured to assign pieces of source data to annotators, receive annotations associated with pieces of source data from annotation devices, generate source data metadata and annotator metadata using the received annotations, and estimate the ground truth for pieces of source data. A distributed data annotation server system in accordance with an embodiment of the invention is conceptually illustrated in FIG. 2. The distributed data annotation server system 200 includes a processor 210 in communication with volatile memory 220 and non-volatile memory 230. The distributed data annotation server system 200 also includes a network interface 240 configured to send and receive data over a network connection. In a number of embodiments, the network interface 240 is in communication with the processor 210, the non-volatile memory 230, and the volatile memory 220.

In several embodiments, non-volatile memory is any form of non-volatile storage configured to store a variety of data, including, but not limited to, source data 234, source data metadata 235, annotator metadata 236, and annotations 237. In many embodiments, source data 234, source data metadata 235, annotator metadata 236, and/or annotations 237 are stored using an external server system and received by the distributed data annotation server system 200 using a network interface 240. External server systems in accordance with a variety of embodiments include, but are not limited to, database systems and other distributed storage services.

In the illustrated embodiment, the non-volatile memory 230 is also configured to store a distributed data annotation application 232 that configure the processor 210 to perform a distributed data annotation process. In many embodiments, the processor 210 is configured to transmit pieces of source data 234 to annotation devices using network interface 240. In a variety of embodiments, a uniform resource locator (URL) or other link to the piece of source data 234 is transmitted. In several embodiments, the processor 210 is configured to create annotation tasks to be transmitted to a distributed task performance service and/or annotation devices using the network interface 240. In a number of embodiments, the processor 210 is configured to determine a cost associated with one or more annotation tasks. In many embodiments, the network interface 240 is configured to receive completed annotation tasks including annotations 237 for one or more pieces of source data. The processor 210 is configured using the distributed data annotation application 232 to generate and/or update source data metadata 235 and/or annotator metadata 236 based on annotations 237 associated with source data 234. In a variety of embodiments, the processor 210 is configured to determine a ground truth value, included in source data metadata 235, for at least one piece of source data in the set of source data 234 using the received annotations 237, source data metadata 235, and/or annotator metadata 236. In a number of embodiments, the processor 210 is configured to update the source data metadata 235 and/or annotator metadata 236 using the determined ground truth value. In several embodiments, the processor 210 is configured to update the ground truth value using updated source data metadata 235 and/or annotator metadata 236.

Distributed data annotation server systems are described above with respect to FIG. 2; however, a variety of architectures, including those which store data or applications on disk or some other form of storage and are loaded into volatile memory 220 at runtime, can be utilized in accordance with embodiments of the invention. Processes for the distributed annotation of pieces of source data in accordance with embodiments of the invention are discussed further below.

Distributed Data Annotation

Figure 3:
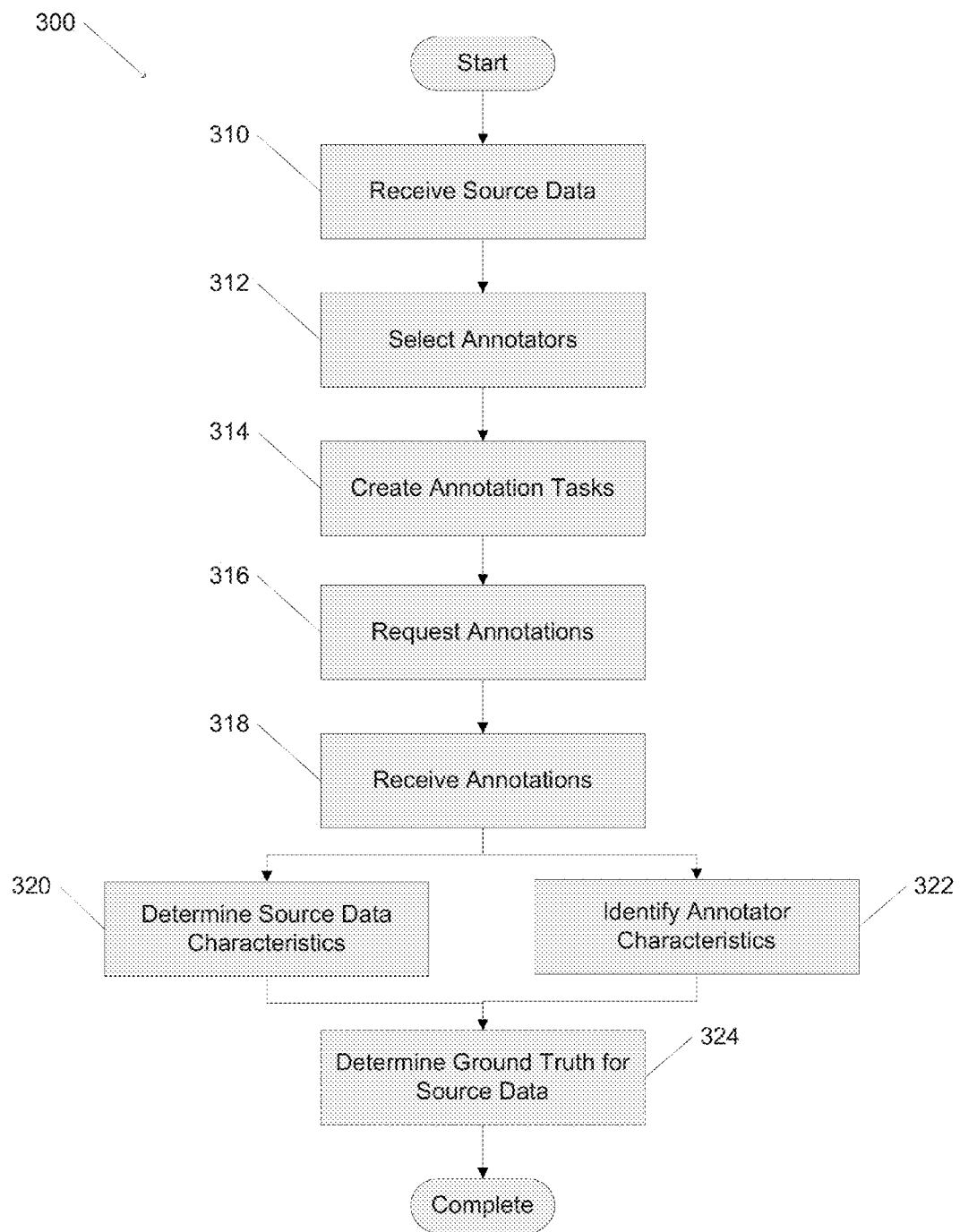
FIG. 3 is a flow chart illustrating a process for the distributed annotation of source data in accordance with an embodiment of the invention.

The distributed annotation of source data involves the annotation of one or more pieces of source data by a number of annotators. Using the annotations, the characteristics of the source data and the competence of the annotators can be determined, and the characteristics of the source data and the competence of annotators can be used to estimate ground truths concerning the source data and/or to improve performance of future distributed data annotation tasks. A process for distributed data annotation in accordance with an embodiment of the invention is illustrated in FIG. 3. The process 300 includes receiving (310) source data. Annotators are selected (312). Annotation tasks are created (314). Annotations are requested (316). Annotations are received (318). Source data characteristics are determined (320). Annotator characteristics are identified (322). In a variety of embodiments, the ground truth for one or more pieces of source data is determined (324).

In many embodiments, the received (310) source data contains one or more pieces of source data, where the pieces of source data can be, but are not limited to, image data, audio data, video data, and text data. The pieces of source data can include source data metadata describing the piece of source data. Source data metadata can include, but is not limited to, one or more annotations applied to the piece of source data, metrics indicative of the difficulty of annotating the piece of source data, features of the source data, and the annotators who have previously annotated the piece of source data. In a number of embodiments, one or more annotators are selected (312) based on the received (310) source data. In several embodiments, metadata describing the annotator is associated with at least one selected (312) annotator. Annotator metadata can include, but is not limited to, metrics indicative of the expertise of the annotator, metrics indicative of the bias of the annotator regarding incorrect annotations of source data, annotations previously provided by the annotator, and data previously annotated by the annotator.

In many embodiments, creating (314) annotation tasks includes creating a human intelligence task for a piece of source data. In several embodiments, creating (314) an annotation task includes targeting one or more annotators based upon the source metadata for the piece of source data in the annotation task, and annotator metadata for the targeted annotators. In several embodiments, creating (314) an annotation task includes determining a reward to be paid for completing the annotation task. The reward can be determined based on the annotator to which the annotation task is assigned and/or the piece of source data contained in the annotation task. In several embodiments, requesting (316) annotations includes submitting created (314) annotation tasks to a human intelligence task marketplace, such as MTurk. In a number of embodiments, creating (314) a annotation task includes creating (314) a machine intelligence task for a piece of source data and requesting (316) annotations includes submitting the machine intelligence task to an annotation device configured to perform machine intelligence tasks. In many embodiments, creating (314) a machine intelligence task includes determining a charge to perform the machine intelligence tasks. In several embodiments, distributed data annotation server systems are configured to optimize the cost of annotating a set of received (310) source data based on the costs of performing human intelligence tasks and machine intelligence tasks. In a number of embodiments, machine intelligence tasks and human intelligence tasks may involve one or more pieces of source data. In a variety of embodiments, created (314) annotation tasks are binary annotation tasks. In several embodiments, created (314) annotation tasks are multidimensional annotation tasks. In many embodiments, created (314) annotation tasks are free-form annotation tasks.

In several embodiments, the received (318) annotations include a label describing the piece of source data targeted in the requested (316) annotation. In a number of embodiments, one or more annotations are received (318) for a particular piece of source data. The received (318) annotations can be from a human intelligence task marketplace and/or results received from an annotation device configured to perform machine intelligence tasks.

In many embodiments, determining (320) source data characteristics includes creating or updating metadata associated with the piece of source data annotated by one or more of the received (318) annotations. In several embodiments, determining (320) source data characteristics includes determining a confidence value related to the received (318) annotations depending on the annotator of the requested (316) annotation task and/or other annotations received (318) for the piece of source data. In a variety of embodiments, identifying (322) annotator characteristics includes creating or updating annotator metadata associated with an annotator. In many embodiments, identifying (322) annotator characteristics includes comparing annotations received (318) from that annotator with the source data characteristics determined (320) for source data annotated by the annotator. In several embodiments, identifying (322) annotator characteristics includes comparing the annotations received (318) from an annotator across a variety of pieces of source data. In a number of embodiments, identifying (322) annotator characteristics includes comparing the received (318) annotations from one annotator against annotations for source data received (318) from a variety of other annotators. In many embodiments, determining (320) source data characteristics and/or identifying (322) annotator characteristics utilizes one or more statistical techniques. A variety of statistical techniques can be utilized in accordance with embodiments, of the invention, including, but not limited to, gradient descent, gradient ascent, expectation-maximization, and maximum a posteriori techniques. Statistical techniques for determining source data characteristics and/or identifying annotator characteristics in accordance with embodiments of the invention are discussed further below. In many embodiments, determining (320) source data characteristics and/or identifying (322) annotator characteristics are determined iteratively. In several embodiments, iteratively determining (320) source data characteristics and/or identifying (322) annotator characteristics includes refining the source data characteristics and/or annotator characteristics based upon prior refinements to the source data characteristics and/or annotator characteristics. In a number of embodiments, iteratively determining (320) source data characteristics and/or identifying (322) annotator characteristics includes determining a confidence value for the source data characteristics and/or annotator characteristics; the iterations continue until the confidence value for the source data characteristics and/or annotator characteristics exceeds a threshold value. The threshold value can be pre-determined and/or determined based upon the confidence necessary for a particular application.

In a variety of embodiments, determining (324) the ground truth for one or more pieces of source data utilizes the determined (320) source data characteristics and/or the identified (322) annotator characteristics. In a number of embodiments, source data characteristics have not been determined (320) and/or annotator characteristics have not been identified (324). When source data characteristics and/or annotator characteristics are not available, the ground truth for a piece of data can be determined (324) in a variety of ways, including, but not limited to, providing a default set of source data characteristics and/or annotator characteristics and determining the ground truth. In a number of embodiments, the default annotator characteristics indicate annotators of average competence. In certain embodiments, the default annotator characteristics indicate annotators of excellent competence. In several embodiments, the default annotator characteristics indicate an incompetent annotator. In many embodiments, the default annotator characteristics indicate an adversarial annotator. A number of processes can be utilized in accordance with embodiments of the invention to determine (324) the ground truth for a piece of source data, including, but not limited to, using the weighted sum of the annotations for a piece of source data as the ground truth, where the annotations are weighted based on the competence of the annotators. As is discussed further below, the difficulty of annotating source data and the competence of annotators can be statistically modeled and ground truths for the source data can be determined by optimizing the model based upon the observed annotations of the source data to determine the most likely ground truth for the source data.

Although specific processes for the distributed annotation of source data are discussed above with respect to FIG. 3, any of a variety of processes can be performed in accordance with embodiments of the invention. Processes for refining data determined during the distributed data annotation process, including the ground truth for a piece of source data and the relationships between source data, annotators, and annotated data in accordance with embodiments of the invention are discussed below.

Refining Determined Characteristics

Figure 3B:
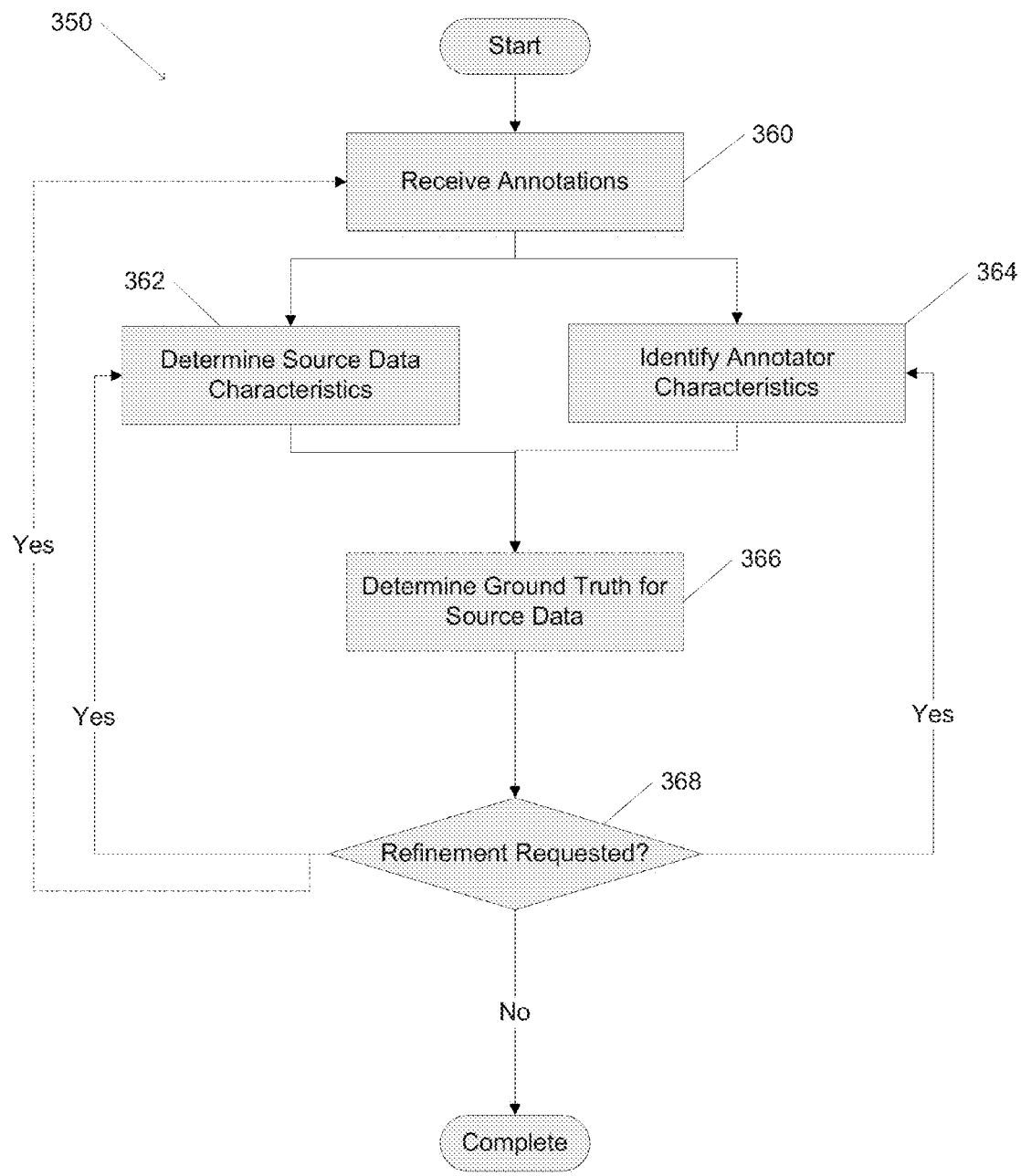
FIG. 3B is a flow chart illustrating a process for refining characteristics determined during the distributed annotation of source data in accordance with an embodiment of the invention.

In a number of embodiments, distributed data annotation server systems are configured to refine source data characteristics, annotator characteristics, and ground truth for one or more pieces of source data as additional characteristics and ground truths are determined. A process for refining information determined during the distributed data annotation process in accordance with an embodiment of the invention is shown in FIG. 3B. The process 360 includes receiving (360) annotations. Source data characteristics are determined (362). Annotator characteristics are identified (364). In several embodiments, the ground truth for one or more pieces of source data is determined (366). A decision is made regarding further refinement. If further refinement is requested (368), updated source data characteristics are determined (362) and/or updated annotator characteristics are identified (364) based one or more of the source data characteristics, annotator characteristics and/or ground truths determined from the previous iteration. In several embodiments, if refinement is requested (368), additional annotations are received (360). If further refinement is not requested (368), the process completes providing the ground truths, source data characteristics, and/or annotator characteristics for use in other applications and/or annotation tasks.

A variety of processes may be utilized to receive (360) annotations, determine (362) source data characteristics, identify (364) annotator characteristics, and determine (366) the ground truth for one or more pieces of source data in accordance with embodiments of the invention, including those described above with respect to FIG. 3. In a number of embodiments, refinement is requested (368) using a confidence value determined using the determined (362) source data characteristics, the identified (364) annotator characteristics, and/or the determined (366) ground truth. If the confidence value is above a threshold value, refinement is not requested (368); if the confidence value is not above the threshold value, refinement is requested (368). In many embodiments, the confidence value is determined by comparing updated determined (362) source data characteristics against previously determined (362) source data characteristics. In a variety of embodiments, the confidence value is determined by comparing updated identified (364) annotator characteristics against previously identified (364) annotator characteristics. In several embodiments, the confidence value is determined by comparing updated determined (366) ground truth information against previously determined (366) ground truth information. A number of other processes may be utilized in accordance with embodiments of the invention to request (368) refinement, including, but not limited to, performing a particular number of refinements when annotations are received (360) and performing one or more estimations using the source data characteristics, annotator characteristics, and/or ground truth information until a threshold value is reached. A variety of statistical estimations may be utilized in accordance with embodiments of the invention.

Although specific processes for refining characteristics determined during the distributed annotation of source data are discussed above with respect to FIG. 3B, any of a variety of processes can be performed in accordance with embodiments of the invention. Relationships between source data, annotators, and annotated data in accordance with embodiments of the invention are discussed below.

Annotators, Annotations, and Source Data

A variety of characteristics can be utilized in accordance with embodiments of the invention to describe annotators, source data, and annotations applied to source data. These characteristics may be determined utilizing a variety of probabilistic techniques. Conceptual illustrations of source data metadata, annotator metadata, and annotations utilized by distributed data annotation systems in accordance with embodiments of the invention are shown in FIGS. 4A, 4B, and 4C.

Figure 4A:
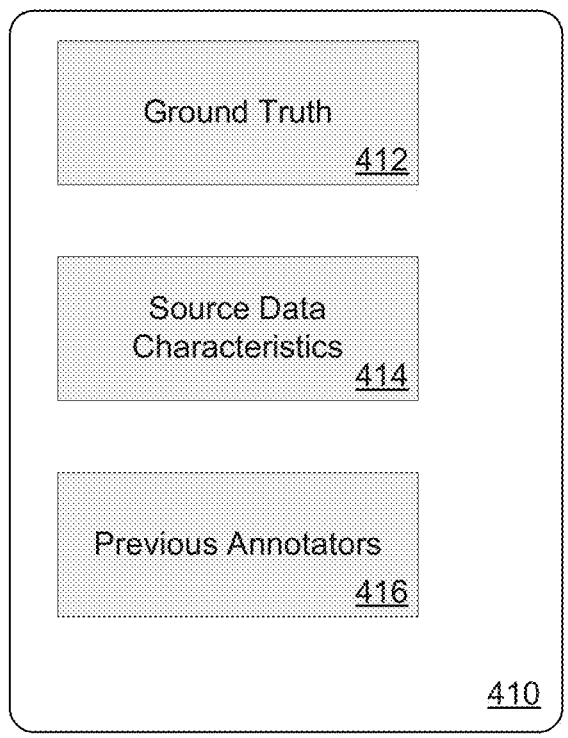
FIG. 4A is a conceptual model of a piece of source data utilized in a distributed data annotation system in accordance with an embodiment of the invention.

Turning now to FIG. 4A, source data metadata 410 describes the properties of a piece of source data and includes ground truth information 412, source data characteristics 414, and a record of previous annotators 416 for the piece of source data. Ground truth information 412 describes the content contained in the piece of source data corresponding source data metadata 410; the ground truth information 412 may or may not correspond to the true content of the piece of source data. The ground truth information 412 is the best estimate of the ground truth based upon annotations of the source data. In the illustrated embodiment, the source data metadata 410 also contains a record 416 of the annotators that have previously annotated the source data metadata 410. In a number of embodiments, the record of previous annotators 416 is a reference to one or more pieces of annotator metadata stored in an annotator metadata database. In many embodiments, source data metadata 410 is stored in a source data metadata database.

Source data characteristics 414 describe characteristics of the source data and can be utilized in determining the difficulty of annotating the source data. Source data characteristics 414 for image data include, but are not limited to, the specimen captured in the image, the location of the image, the viewpoint of the image, the pose of the image, the weather captured in the image, the camera angle of the image, the height of the image, and the color or colors in the image. In a number of embodiments, the source data is a multi-dimensional embedding of images and the source data characteristics 414 include, but are not limited to, the height of an image in the multi-dimensional embedding and the color of an image in the multi-dimensional embedding. Other source data characteristics 414 for other kinds of source data may include other factors not specifically listed above and/or a variety of factors appropriate to the requirements of the specific application. The source data characteristics 414 may be influenced by a random amount of variability in the creation of the source data metadata 410. In a variety of embodiments, one or more of the source data characteristics 414 are weighted. Source data characteristics weights are determined using a variety of techniques, including, but not limited to, using an ideal annotator, using an adversarial annotator, using an ordinary annotator, and using a combination of annotators.

Figure 4B:
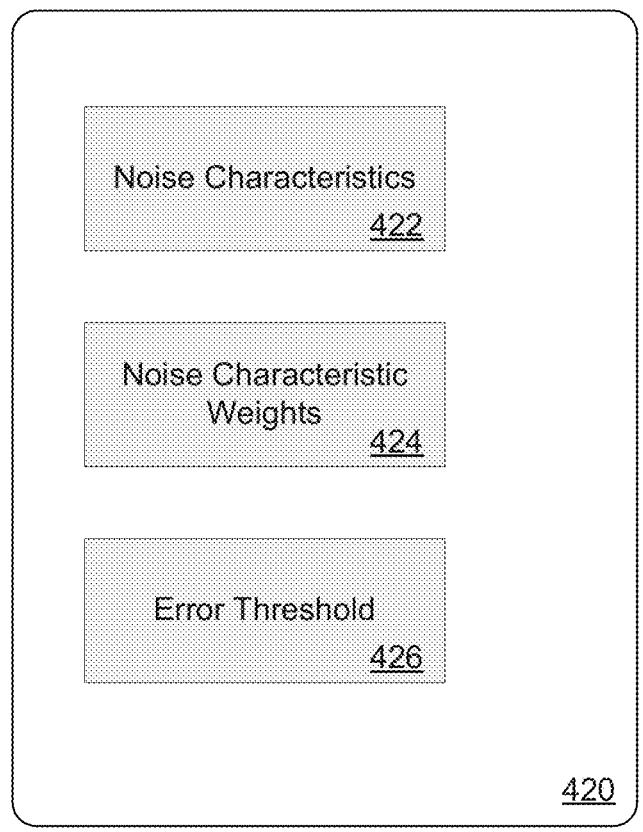
FIG. 4B is a conceptual model of an annotator utilized in a distributed data annotation system in accordance with an embodiment of the invention.
Figure 4C:
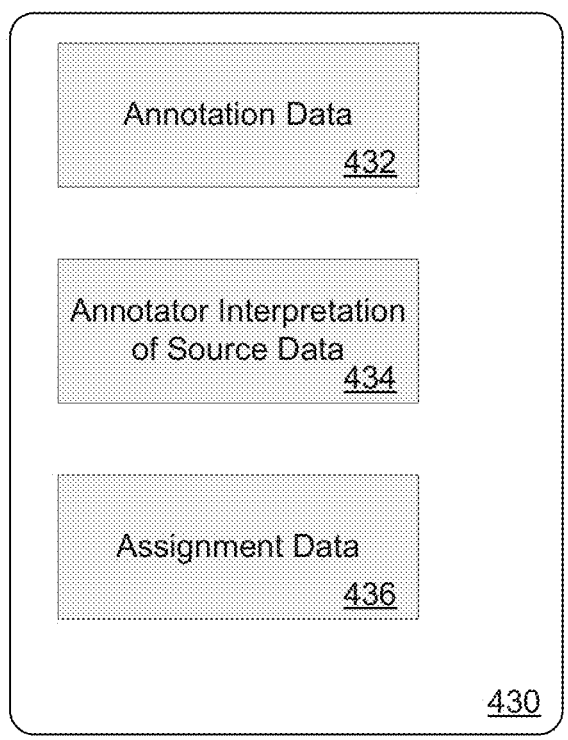
FIG. 4C is a conceptual model of an annotation utilized in a distributed data annotation system in accordance with an embodiment of the invention.

Turning now to FIG. 4B, annotator metadata 420 is illustrated that describes the properties of an annotator and includes noise characteristics 422, noise characteristics weights 424, and an error threshold 426. Noise characteristics 422 are a description of how the annotator annotates a piece of source data. Noise characteristics 422 can be modeled depending on a variety of factors including, but not limited to, the type of source data being annotated. For image data, noise characteristics 422 include, but are not limited to, visual acuity, attention to the task at hand, direction of gaze, and knowledge of the subject matter being annotated. Noise characteristics 422 for other kinds of source data may include other factors not specifically listed above and/or a variety of factors appropriate to the requirements of the specific application. Noise characteristics 422 can vary between annotators for a particular piece of source data and can vary for the same annotator between different pieces of source data. The competency of the annotator described using annotator metadata 420 can be determined utilizing the noise characteristics 422; a competent annotator may have a noise characteristic 422 above or below a threshold value that can be pre-determined or determined dynamically. Annotator metadata 420 further includes noise characteristics weights 424; the noise characteristics weights 424 describe how the annotator utilizes one or more of the noise characteristics 422 in annotating a piece of source data.

An annotator's interpretation of the ground truth of a piece of source data in view of the noise characteristics 422 and noise characteristic weights 424 may not correspond to the actual ground truth of the piece of source data in reality, resulting in incorrect annotations being generated by the annotator. Annotator metadata 420 includes an error threshold 426 describing the annotator's bias towards annotation errors. Error threshold 426, in combination with the annotator's interpretation of a piece of source data, is utilized to determine the annotation the annotator will generate for a piece of source data. In a variety of embodiments, the error threshold 426 describes if the annotator is disposed towards false positives or false negatives in the annotation of a piece of source data.

In several embodiments, annotators may be described according to the noise characteristics 422, noise characteristic weights 424, and error threshold 426 in annotator metadata 420. "Ideal" annotators are annotators who are not influenced by noise characteristics 422, such that ideal annotators correctly annotate source data. In many embodiments, ideal annotators have noise characteristic weights 424 of zero for each noise characteristic 422. Conversely, "adversarial" annotators are annotators who identify correct annotations for source data; however, adversarial annotators sometimes or always provide incorrect annotations for source data. Adversarial annotators may be described as having an error threshold 426 that causes the annotator to provide incorrect annotations despite correctly identifying correct annotations. "Ordinary" annotators are annotators who try and correctly annotate source data, however, due to noise and/or error thresholds, may make mistakes in some annotations. Ordinary annotators have at least one noise characteristic 422, at least one non-zero noise characteristic weight 424, and/or an error threshold 426 which causes the annotator to provide false positive and/or false negative annotations.

Turning now to FIG. 4C, annotation 430 for a piece of source data includes annotation data 432, the annotator interpretation of source data 434, and assignment data 436. Annotation data 432 is the label and/or other identification generated by an annotator for a piece of source data. The interpretation 434 is the view the annotator took regarding the piece of source data when generating the annotation 430 based upon the characteristics of the annotator and the characteristics of the piece of source data. Assignment data 436 indicates which annotator generated the annotation data 432 and the piece of source data to which annotation 430 applies. In many embodiments, annotators assign annotations 430 to a source data metadata 410 using a linear classifier. In a variety of embodiments, annotations 430 are stored in a source data database and/or a distributed data annotation server system.

Specific pieces of source data, annotators, and annotations are described above with respect to FIGS. 4A, 4B, and 4C; however, a variety of characteristics may be assigned to pieces of source data, annotators, and annotations, and a variety of statistical techniques may be utilized in accordance with embodiments of the invention. Processes for determining source data characteristics and annotator characteristics in accordance with embodiments of the invention are discussed below.

Determining Source Data and Annotator Characteristics

As described above with respect to FIG. 3, the characteristics described by source data metadata 410 and the noise characteristics described by annotator metadata 420 can be determined using only the annotation data 432 and a variety of statistical techniques. In several embodiments, the probability of a specific set of source data characteristics, noise characteristics for an annotator, and error thresholds for an annotator given a specific set of annotations for a set of source data can be determined as follows:

$$p(\mathcal{L}, x, w, \tau) = \prod_{j=1}^{M} p(\tau_j | \gamma) p(w_j | \alpha) \prod_{i=1}^{N} \left( p(x_i | \theta_z, \beta) \prod_{j \in \mathcal{J}_i} p(l_{ij} | x_i, w_j, \tau_j) \right)$$

where M is the number of annotators indexed by j, N is the number of pieces of source data index by i, $\mathcal{L}$ and $l_{ij}$ are the labels provided by one or more annotators for the piece of source data, x and $x_i$ are source data characteristics 414 for a piece of source data, w and $w_j$ are noise characteristic weights for annotator j, $\tau$ and $\tau_j$ are the error thresholds for annotator j, $\gamma$ and $\alpha$ are Gaussian priors used during the inference of $w_j$ and $\tau_j$, z is the ground truth for a piece of source data, $\beta$ is Bernoulli prior on z with standard deviation $\theta_z$. In a variety of embodiments, other priors may be utilized according the requirements of specific applications. In several embodiments, $\beta=0.5$ and $\theta_x=0.8$.

In many embodiments, x, w, and $\tau$ are solved by finding the maximum a posteriori estimation of the optimal parameters x*, w*, and $\tau$*, given by the equation $$(x^*, w^*, \tau^*) = \operatorname*{argmax}_{x,w,\tau} p(|x, w, \tau|\mathcal{L}) = \operatorname*{argmax}_{x,w,\tau} m(x, w, \tau)$$

and $$m(x, w, \tau) = \log p(\mathcal{L}, x, w, \tau)$$

In a number of embodiments, m(x,w,$\tau$) is maximized using the following formula:

$$m(x, w, \tau) = \sum_{i=1}^{N} \log p(x_i | \theta_z, \beta) + \sum_{j=1}^{M} \log p(w_j | \alpha) + \sum_{j=1}^{M} \log p(\tau_j | \gamma) + \sum_{i=1}^{N} \sum_{j \in \mathcal{J}_i} [l_{ij} \log \Phi((w_j, x_i) - \tau_j) + (1 - l_{ij}) \log(1 - \Phi((w_j, x_i) - \tau_j))]$$

where $\Phi(\bullet)$ is the cumulative standardized normal distribution. In a variety of embodiments, $\Phi(\bullet)$ is any sigmoidal-shaped function. In other embodiments, any function appropriate to the requirements of a specific application can be utilized. In many embodiments, maximizing m(x,w,$\tau$) is performed using gradient ascent, alternating between fixing the parameters associated with a piece of source data and the parameters associated with an annotator. Fixing the parameters in this way corresponds to initially determining estimates of the ground truth and the difficulty of characterizing the source data, using the initial estimates of the ground truths and difficulty of characterizing the source data to characterize the competence of the annotators, and then updating the estimates of the ground truth and difficulty of characterizing the source data by weighting the annotations provided by the annotators based upon competence. A process of determining ground truths and difficulty and using these determinations to determine annotator competence for updating the ground truths can be repeated until a termination condition is satisfied. In several embodiments, the repetitions of gradient ascent are repeated until $m(x,w,\tau)$ is determined within a threshold value; the threshold value may be pre-determined or determined dynamically. Other statistical maximization and/or minimization techniques may be utilized in accordance with embodiments of the invention.

In several embodiments, the sensitivity d' of an annotator to noise characteristics 422 is given by the Mahalanobis distance between $\mu_0$ and $\mu_1$ normalized by s:

$$d' = \frac{\mu_1 - \mu_0}{s} = \frac{2}{\sqrt{\theta_2^2 + \sigma_j^2}}$$

where d' is an indicator of how observant an annotator is to the source data characteristics 414 of a source data metadata 410 and $\mu_0$ and $\mu_1$ are the centers for $z_i=0$ and $z_i=1$ for the normal distribution $$p(y_{ij}|z_i) = N(y_{ij}|\mu_z, s^2)$$

with variance $$s^2 = \theta_z^2 + \sigma_j^2$$

A variety of other distance determination techniques may be utilized in accordance with many embodiments of the invention.

In a number of embodiments, the sensitivity d' of an annotator to noise characteristics 422 is determined using false alarm rate f and hit rate h by the equation $$d' = \Phi^{-1}(h) = \Phi^{-1}(f)$$

where $\Phi^{-1}$ is the inverse of the cumulative normal distribution described above. In a number of embodiments, a variety of distributions may be utilized. In several embodiments, a variety of other processes may be utilized to describe the sensitivity of an annotator to noise characteristics 422.

In many embodiments, the error threshold 426 for an annotator is determined using the equation:

$$\lambda = -\frac{1}{2}(\Phi^{-1}(h) + \Phi^{-1}(f))$$

where $\lambda$ is the error threshold 426. In a variety of embodiments, a large positive $\lambda$ indicates that an annotator attributes a high cost to false positives, while a large negative $\lambda$ indicates that the annotator avoids false negatives. In several embodiments, $\lambda$ is related to $\tau_j$; in a variety of embodiments, $\lambda = \tau_j/s$.

Specific processes for determining annotator, source data, and annotation characteristics are described above in accordance with embodiments of the invention; however, a variety of processes and statistical techniques may be utilized in accordance with embodiments of the invention. Although the present invention has been described in certain specific aspects, many additional modifications and variations would be apparent to those skilled in the art. It is therefore to be understood that the present invention can be practiced otherwise than specifically described without departing from the scope and spirit of the present invention. Thus, embodiments of the present invention should be considered in all respects as illustrative and not restrictive. Accordingly, the scope of the invention should be determined not by the embodiments illustrated, but by the appended claims and their equivalents.

What is claimed is:

1. A system comprising:
   a memory configured to store source data, at least one annotator, annotation tasks, and a distributed data annotation application; and
   a processor;
   wherein the distributed data annotation application configures the processor to:
      receive a set of source data, where the source data comprises at least one piece of source data;
      select at least one annotator for at least one piece of source data;
      create at least one annotation task for the selected annotators and the at least one piece of source data;
      request at least one annotations for the at least one piece of source data using the created annotation tasks;
      receive annotations for the at least one piece of source data; and
      generate annotator metadata for at least one annotator using an iterative maximum a posteriori estimation based on the received annotations and at least one piece of source data, wherein the annotator metadata describes annotator characteristics;
      determine source data metadata for at least one piece of source data using the received annotations, where the source data metadata comprises source data characteristics; and
      estimate a ground truth for at least one piece of source data using the source data metadata and the annotator metadata by iteratively:
         updating source data metadata for at least one piece of source data based on at least the previously determined source data metadata and annotator metadata;
         updating annotator metadata for at least one annotator based on at least the previously determined source data metadata and annotator metadata; and
         estimating the ground truth for at least one piece of source data using the updated source data metadata and the updated annotator metadata when a termination condition occurs.

2. The system of claim 1, wherein the iterative maximum a posteriori estimation is selected from the group consisting of gradient ascent, gradient descent, and estimation-maximization.

3. The system of claim 1, wherein the distributed data annotation application further configures the processor to determine a confidence threshold value regarding the ground truth of at least one piece of source data.

4. The system of claim 1, wherein the distributed data annotation application further configures the processor to update source data metadata for at least one piece of source data using the received annotations and the annotator metadata.

5. The system of claim 4, wherein the source data metadata includes a measure of the difficulty of describing the source data.

6. The system of claim 5, wherein the source data metadata further comprises source data characteristics selected from the group consisting of annotations applied to the piece of source data, features of the source data, and annotators who have previously annotated the piece of source data.

7. The system of claim 1, wherein the distributed data annotation application further configures the processor to update annotator metadata for at least one annotator using the received annotations and the source data metadata.

8. The system of claim 7, wherein the annotator metadata includes a measure of competence of the annotator.

9. The system of claim 8, wherein the annotator metadata further comprises annotator characteristics selected from a group consisting of an expertise of the annotator, bias of the annotator regarding mislabeling of source data, annotations previously provided by the annotator, and references to source data previously annotated by the annotator.

10. The system of claim 1, wherein selecting at least one annotator for at least one piece of source data comprises selecting at least one annotator based on at least one source data characteristic in the source data metadata.

11. The system of claim 1, wherein the distributed data annotation application further configures the processor to determine a cost for performing the annotation task.

12. The system of claim 1, wherein:
the annotation task is a human intelligence task; and
the distributed data annotation application further configures the processor to request at least one annotations by submitting at least one annotation task to a human intelligence task marketplace.

13. The system of claim 1, wherein:
the annotation task is a machine intelligence task; and
the distributed data annotation application further configures the processor to request at least one annotations by submitting at least one annotation task to an annotation device configured to perform machine intelligence tasks.

14. The system of claim 1, wherein selecting at least one annotator for at least one piece of source data comprises selecting at least one annotator based on at least one annotator characteristic in the annotator metadata describing the at least one annotator.

15. A method, comprising:
receiving a set of source data using a distributed data annotation server system, where the set of source data comprises at least one pieces of source data;
selecting at least one annotator for at least one piece of source data using the distributed data annotation server system;
creating at least one annotation tasks for the selected annotators and the at least one piece of source data using the distributed data annotation server system;
requesting at least one annotations for the at least one piece of source data using the created annotation tasks and the distributed data annotation server system;
receiving annotations for the at least one piece of source data using the distributed data annotation server system; and
generating annotator metadata for at least one annotator using an iterative maximum a posteriori estimation based on the received annotations, at least one piece of source data, and the distributed data annotation server system, wherein the annotator metadata describes annotator characteristics;
determining source data metadata for at least one piece of source data based on the received annotations using the distributed data annotation server system, where the source data metadata comprises source data characteristics; and
estimate a ground truth for at least one piece of source data based on the source data metadata and the annotator metadata using the distributed data annotation server system by iteratively:
updating source data metadata for at least one piece of source data based on at least the previously determined source data metadata and annotator metadata;
updating annotator metadata for at least one annotator based on at least the previously determined source data metadata and annotator metadata; and
estimating the ground truth for at least one piece of source data using the updated source data metadata and the updated annotator metadata when a termination condition occurs.

16. The method of claim 15, further comprising updating source data metadata for at least one piece of source data using the received annotations, the annotator metadata, and the distributed data annotation server system.

17. The method of claim 15, further comprising updating annotator metadata for at least one annotator using the received annotations, the source data metadata, and the distributed data annotation server system.

18. The method of claim 15, further comprising determining a confidence threshold value regarding the ground truth of at least one piece of source data using the distributed data annotation server system.

19. The method of claim 15, further comprising determining a cost for performing the annotation task using the distributed data annotation server system.

20. The method of claim 15, wherein:
the annotation task is a human intelligence task; and
requesting at least one annotations further comprises submitting at least one annotation task to a human intelligence task marketplace using the distributed data annotation server system.

21. The method of claim 15, wherein:
the annotation task is a machine intelligence task; and
requesting at least one annotations further comprises submitting at least one annotation task to an annotation device using the distributed data annotation server system, where the annotation device is configured to perform machine intelligence tasks.

* * * * *